(12) United States Patent
Broome

(10) Patent No.: US 8,070,769 B2
(45) Date of Patent: Dec. 6, 2011

(54) INVERTED EMBOLIC PROTECTION FILTER

(75) Inventor: Thomas E. Broome, Shakopee, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 989 days.

(21) Appl. No.: 10/139,891

(22) Filed: May 6, 2002

(65) Prior Publication Data
US 2003/0208224 A1  Nov. 6, 2003

(51) Int. Cl.
*A61M 29/00* (2006.01)
(52) U.S. Cl. .................................................. 606/200
(58) Field of Classification Search .................... 606/200
See application file for complete search history.

(56) References Cited

U.S. PATENT DOCUMENTS

| | | | |
|---|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,590,938 A | 5/1986 | Segura et al. |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,842,579 A | 6/1989 | Shiber |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |

(Continued)

FOREIGN PATENT DOCUMENTS
DE        28 21 048        7/1980
(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner* — S. Thomas Hughes
*Assistant Examiner* — Thomas McEvoy
(74) *Attorney, Agent, or Firm* — Seager, Tufte & Wickhem, LLC

(57) ABSTRACT

An embolic protection filter having an inverted membrane with improved blood perfusion characteristics is disclosed. An embolic protection filter in accordance with the present invention comprises a filter frame disposable about a guidewire, a support hoop coupled to a plurality of expandable struts, and an inverted membrane for filtering embolic debris. The inverted membrane has a tapered proximal section and an enlarged diameter distal section. Features of the present invention permit the perfusion of blood through the filter irrespective of embolic debris entrained therein.

18 Claims, 1 Drawing Sheet

U.S. PATENT DOCUMENTS

| | | | |
|---|---|---|---|
| 5,102,415 A | 4/1992 | Guenther et al. | |
| 5,133,733 A | 7/1992 | Rasmussen et al. | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,224,953 A | 7/1993 | Morgentaler | |
| 5,329,942 A | 7/1994 | Gunther et al. | |
| 5,330,484 A | 7/1994 | Gunther | |
| 5,354,310 A | 10/1994 | Garnie et al. | |
| 5,376,100 A | 12/1994 | Lefebvre | |
| 5,421,832 A | 6/1995 | Lefebvre | |
| 5,423,742 A | 6/1995 | Theron | |
| 5,449,372 A | 9/1995 | Schmaltz et al. | |
| 5,456,667 A | 10/1995 | Ham et al. | |
| 5,462,529 A | 10/1995 | Simpson et al. | |
| 5,536,242 A | 7/1996 | Willard et al. | |
| 5,549,626 A | 8/1996 | Miller et al. | |
| 5,658,296 A | 8/1997 | Bates et al. | |
| 5,662,671 A | 9/1997 | Barbut et al. | |
| 5,695,519 A | 12/1997 | Summers et al. | |
| 5,720,764 A | 2/1998 | Naderlinger | |
| 5,728,066 A | 3/1998 | Daneshvar | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Bouewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A * | 9/1998 | Daniel et al. | 606/200 |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,848,964 A | 12/1998 | Samuels | |
| 5,876,367 A | 3/1999 | Kaganov et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,605 A | 7/2000 | Barbut et al. | |
| 6,117,154 A | 9/2000 | Barbut et al. | |
| 6,129,739 A | 10/2000 | Khosravi | |
| 6,136,016 A | 10/2000 | Barbut et al. | |
| 6,142,987 A | 11/2000 | Tsugita | |
| 6,146,396 A | 11/2000 | Konya et al. | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,025 B1 * | 4/2001 | Thistle et al. | 606/200 |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 * | 8/2001 | Levinson et al. | 606/200 |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 * | 2/2002 | Levinson et al. | 606/200 |
| 6,346,116 B1 * | 2/2002 | Brooks et al. | 606/200 |
| 6,361,545 B1 * | 3/2002 | Macoviak et al. | 606/200 |
| 6,391,044 B1 * | 5/2002 | Yadav et al. | 606/200 |
| 6,485,501 B1 * | 11/2002 | Green | 606/200 |
| 6,517,559 B1 * | 2/2003 | O'Connell | 606/158 |
| 6,540,722 B1 * | 4/2003 | Boyle et al. | 604/106 |
| 6,605,102 B1 * | 8/2003 | Mazzocchi et al. | 606/200 |
| 6,635,070 B2 * | 10/2003 | Leeflang et al. | 606/200 |
| 6,837,898 B2 * | 1/2005 | Boyle et al. | 606/200 |
| 7,491,215 B2 * | 2/2009 | Vale et al. | 606/200 |
| 2001/0044634 A1 * | 11/2001 | Michael et al. | 606/200 |
| 2002/0042627 A1 | 4/2002 | Brady et al. | |
| 2002/0123766 A1 * | 9/2002 | Seguin et al. | 606/200 |
| 2002/0138094 A1 * | 9/2002 | Borillo et al. | 606/200 |
| 2003/0130684 A1 * | 7/2003 | Brady et al. | 606/200 |
| 2003/0163158 A1 * | 8/2003 | White | 606/200 |
| 2003/0176884 A1 * | 9/2003 | Berrada et al. | 606/200 |
| 2003/0187495 A1 * | 10/2003 | Cully et al. | 623/1.15 |
| 2004/0254601 A1 * | 12/2004 | Eskuri | 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| EP | 1 247 500 A2 | 2/2002 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |

| | | |
|---|---|---|
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70325 A2 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

INVERTED EMBOLIC PROTECTION FILTER

FIELD OF THE INVENTION

The present invention relates generally to the field of embolic protection devices. More specifically, the present invention pertains to embolic protection filters having improved blood perfusion characteristics.

BACKGROUND OF THE INVENTION

Intravascular filters such as embolic protection filters are generally placed within a body lumen, such as an artery or vein, downstream of a therapeutic site to filter embolic debris from the blood stream. Examples of therapeutic procedures employing such filters include angioplasty, atherectomy, thrombectomy and stent placement. In a typical procedure, a guidewire is transluminally inserted into the patient and placed across the site of the lesion. An embolic protection filter is then advanced along the guidewire and placed distal the lesion. A therapeutic device such as a dilatation or atherectomy catheter is then advanced along the guidewire and placed proximal the therapeutic site to perform the procedure. The therapeutic device is then engaged, forcing the embolic debris to become dislodged from the walls of the vessel and flow downstream towards the distal vasculature, where it is collected and stored by the filter.

There are numerous types of interventional devices adapted to collect embolic debris released into the blood stream during a therapeutic procedure. Typically, these devices contain a mesh or microporous membrane attached to a support structure having struts, wires, and/or ribs that support the filter within a blood vessel when deployed. Generally, the shape of these filters include a proximal mouth or opening that tapers distally to a closed end portion. Examples of such configurations include baskets, parachutes, or sleeves. In a typical application, embolic debris enters the proximal end of the device, and flows distally where it is stored at the closed end portion of the filter.

Depending on the amount of embolic debris dislodged from the vessel wall, the embolic protection filter may become partially or fully occluded throughout the course of the therapeutic procedure. As a result of the buildup of embolic debris within the filter, the perfusion of blood through the filter diminishes over time.

SUMMARY OF THE INVENTION

The present invention relates generally to the field of embolic protection devices. More specifically, the present invention pertains to embolic protection filters having improved blood perfusion characteristics. In an exemplary embodiment of the present invention, an inverted embolic protection filter comprises a filter frame disposable about a guidewire, a support hoop coupled to a plurality of expandable struts adapted to expand in an outward direction within a body lumen, and an inverted membrane for filtering embolic debris, the inverted membrane having a tapered proximal section and an enlarged diameter distal section. The inverted membrane can be configured such that the perfusion of blood through the filter remains relatively constant irrespective of the amount of embolic debris collected therein.

DETAILED DESCRIPTION OF THE INVENTION

Figure 1:
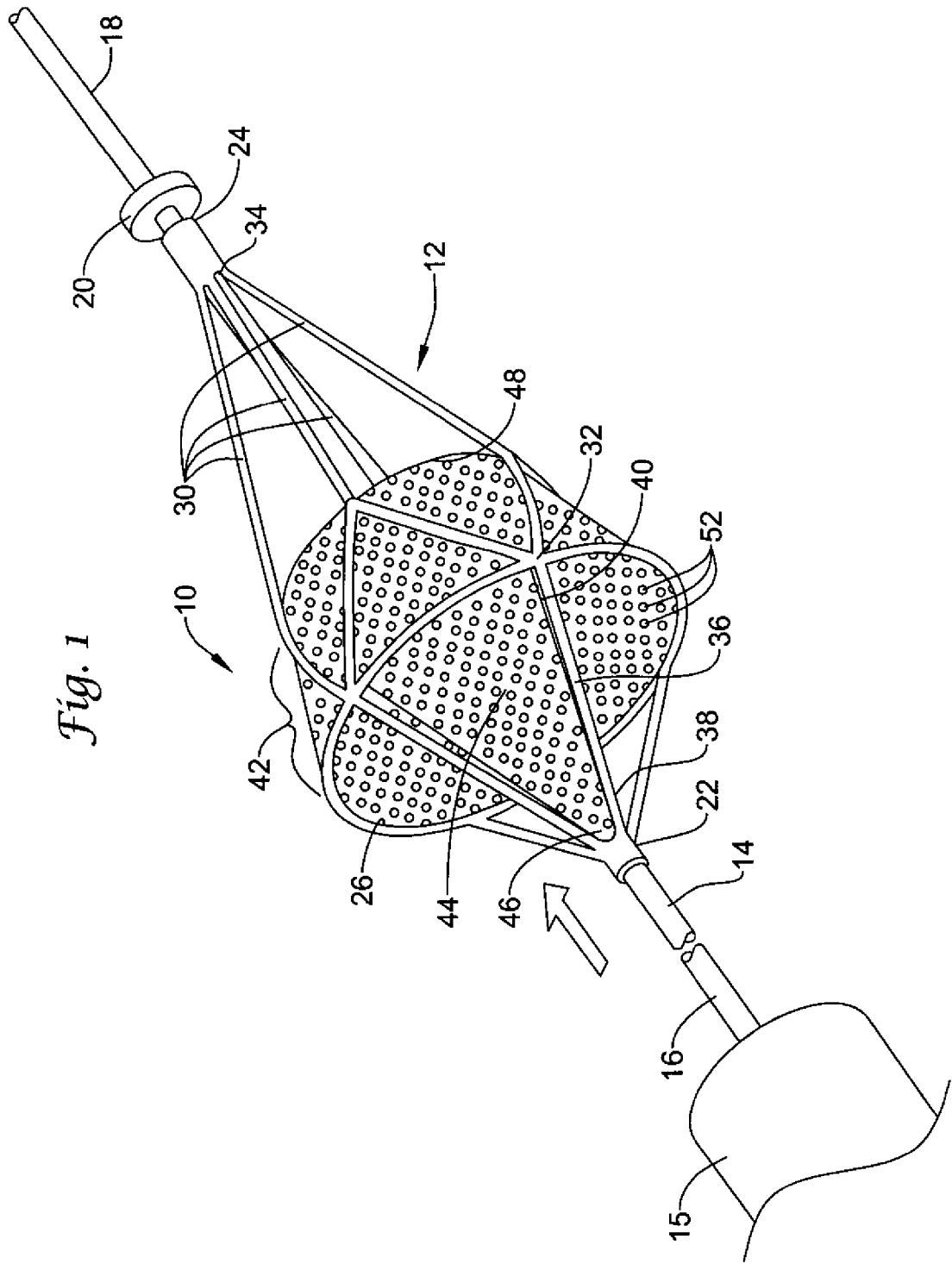
FIG. 1 is a perspective view of an inverted embolic protection filter in accordance with an embodiment of the present invention showing the filter in a radially deployed position.

FIG. 1 is a perspective view of an inverted embolic protection filter 10 in accordance with an exemplary embodiment of the present invention. As shown in FIG. 1, embolic protection filter 10 includes a filter frame 12 disposed about a guidewire 14. Guidewire 14 has a proximal end 16, a distal end 18, and a distal stop 20. Filter frame 12 comprises a first tubular member 22 disposable about guidewire 14, and a second tubular member 24 disposable about guidewire 14 distal the first tubular member 22.

In the exemplary embodiment illustrated in FIG. 1, embolic protection filter 10 is slidably and rotationally disposed about guidewire 14. The first tubular member 22 and second tubular member 24 each define a lumen (not shown) having an inner diameter that is slightly larger than the outer diameter of the guidewire 14, thereby permitting the embolic protection filter 10 to freely slide and rotate about the guidewire 14. An optional coating may be applied to the inner diameter of each tubular member 22, 24 and/or the guidewire 14 to provide a smooth, lubricious surface to facilitate movement of the embolic protection filter 10 along the guidewire 14. For example, a polymeric material such as polytetrafluoroethylene (PTFE) can be applied to the tubular members 22, 24 and/or the outer surface of the guidewire 14.

In an alternative implementation (not shown), embolic protection filter 10 may be secured to the guidewire 14 prior to insertion into the patient's vessel. In this configuration, the first tubular member 22 is secured to the guidewire 14, whereas the second tubular 24 is movably disposed along the guidewire 14. Attachment of the first tubular member 22 to the guidewire 14 may be accomplished by any number of suitable attachment means such as crimping, soldering, bonding, welding, brazing or any combination thereof.

Filter frame 12 can further include a support hoop 26 coupled to a plurality of self-expanding struts 30. Each of the expandable struts 30 is attached at a proximal portion 32 to the support hoop 26, and at a distal portion 34 to the second tubular member 24. The self-expanding struts 30 are biased to self-expand in an outward direction, and can be utilized to deploy the support hoop 26 within a body lumen. In addition, the support hoop 26 may include a preformed shape that facilitates radial deployment (and subsequent removal) of the device within the lumen. For example, the support hoop 26 may include one or more reduced diameter portions disposed about its circumference that permit the support hoop 26 to easily fold or bend into a collapsed position during transport.

To bias the expandable struts 30 in an outward direction, each expandable strut 30 may be pre-formed using a bendable material such as stainless steel or platinum, or a super-elastic material such as nickel-titanium alloy (Nitinol). Nickel-titanium alloy is preferred for its ability to undergo substantial bending or flexing with relatively little residual strain. It is contemplated, however, that other suitable materials can be utilized to bias the expandable struts 30 in an outward direction.

Also attached to support hoop 26 are several optional retrieval struts 36 each having a proximal portion 38 and a distal portion 40. The proximal portion 38 of each retrieval strut 36 is attached to the first tubular member 22. The distal portion 38 of each retrieval strut 36, in turn, is attached to the support hoop 26. The retrieval struts 36 are utilized in the delivery and subsequent retrieval of the embolic protection filter 10. As with the self-expanding struts 30, the retrieval struts 36 are biased to self-expand in an outward direction when unconstrained, and provide additional structural support for the embolic protection filter 10.

Coupled at a proximal end to the first tubular member 22, and extending distally through the mouth formed by support hoop 26, is an inverted membrane 44. In the exemplary embodiment illustrated in FIG. 1, inverted membrane 44 is substantially conical in shape, having a tapered proximal section 46 that extends distally to an enlarged diameter distal section 48. The tapered proximal section 46 of inverted membrane 44 is attached to the first tubular member 22. The enlarged diameter distal section 48 of inverted membrane 44 forms a fold or crease, wherein a length 42 of the inverted membrane 44 folds back and extends proximally towards the support hoop 26.

Inverted membrane 44 can be comprised of a microporous membrane made from a polymeric material such as polypropylene (PP), polyvinylchloride (PVC), polyamide (nylon), polyurethane, polyester, polyethylene tetraphlalate, polyether-ether ketone (PEEK), polyether block amide (PEBA), polytetrafluoroethylene (PTFE) or any mixture, blend or combination thereof Alternatively, inverted membrane 44 can be formed of a mesh screen comprising several woven or braided wires. These woven or braided wires may be made of any number of suitable biocompatible materials such as stainless steel, nickel-titanium alloy or platinum.

Perfusion of blood through the inverted membrane 44 is accomplished through several openings or pores 52 formed in the mesh screen or microporous membrane. The openings or pores 52 are preferably adapted to filter embolic debris contained in the blood stream while substantially permitting the flow of blood therethrough.

In certain embodiments of the present invention, embolic protection filter 10 may include an anti-inflammatory agent to reduce damage to the patient's vascular tract caused during therapeutic the procedure. Examples of such anti-inflammatory agents include dexamethasone, prednisolone, corticosterone, budesonide, estrogen, sulfasalazine, and mesalamine or any suitable combination or mixture thereof. In other embodiments, the embolic protection filter 10 may contain an anti-thrombogenic coating to prevent the formation of clots within the vasculature. Examples of suitable anti-thrombogenic coatings include heparin (and derivatives thereof), urokinase and dextrophenylalanine proline arginine chloromethylketone.

In use, embolic protection filter 10 is advanced distally along guidewire 14 and placed distal a lesion or other occlusion within the patient's vessel. To facilitate transport of the filter 10 through the vessel, a delivery sheath 15 comprising a tubular member having a reduced profile and an inner lumen adapted to transport the embolic protection filter 10 in a collapsed position is advanced through the vessel along the guidewire 14. A distal stop 20 disposed about the distal end 18 of guidewire 14 prevents distal movement of the device thereebeyond. Once the delivery sheath 15 containing the collapsed filter 10 is in place distal the lesion, the delivery sheath 15 is retracted proximally, causing the embolic protection filter 10 to deploy within the vessel as shown in FIG. 1. A therapeutic device such as an angioplasty or atherectomy catheter can then be advanced along the guidewire 14 and placed proximal the lesion. The therapeutic device is then engaged within the vessel, forcing the embolic debris to become dislodged and flow downstream towards the embolic protection filter 10.

As the embolic debris enters the embolic protection filter 10 (as indicated by the arrow in FIG. 1), it is initially deposited on the inverted membrane 44 at or near the tapered proximal section 46. At this location, the velocity of blood flow is generally greatest since it is located at or near the center portion of the vessel. The embolic debris is then deflected distally, where it becomes entrained at or near the fold or crease formed at the enlarged diameter distal section 48. At the enlarged diameter distal section 48, the velocity of the blood flow is generally less than at the tapered proximal section 46 since it is located at or near the vessel wall. Since the embolic debris collects at a location where the velocity of blood flow is generally less, the embolic debris entrained within the embolic protection filter 10 does not substantially interfere with the perfusion of blood through the inverted membrane 44 at or near the tapered proximal section 46. As a result, the flow of blood through inverted membrane 44 remains relatively constant, irrespective of the amount of embolic debris collected by the embolic protection filter 10.

To retrieve embolic protection filter 10 from the body, the delivery sheath 15 is advanced distally along the guidewire 14 until it is proximal the embolic protection filter 10. Continued advancement of the delivery sheath 15 distally causes the portion of the inverted membrane 44 along length 42 to re-invert, allowing the inverted membrane 44, support hoop 26 and support struts 30 to collapse inwardly within the lumen of the delivery sheath 15. Alternatively, when the optional retrieval struts 36 are employed, continued advancement of the delivery sheath 15 against the retrieval struts 36 causes the support hoop 26, support struts 30 and the retrieval struts 36 to collapse inwardly within the lumen of the delivery sheath 15. Once collapsed, the delivery sheath 15 and embolic protection filter 10 containing the collected embolic debris can then be removed from the body.

Having thus described the exemplary embodiments of the present invention, those of skill in the art will readily appreciate that other embodiments may be made and used which fall within the scope of the claims attached hereto. Numerous advantages of the invention covered by this document have been set forth in the foregoing description. It will be understood, however, that this disclosure is, in many respects, only illustrative. Changes may be made in details, particular in matters of shape, size and arrangement of parts without exceeding the scope of the invention.

What is claimed is:

1. An embolic protection filter comprising:
   a filter frame including a proximal tubular member and a distal tubular member disposed about a guidewire;
   wherein the distal tubular member is slidable about the guidewire;
   a support hoop coupled to a plurality of expandable struts, said plurality of expandable struts biased to expand in an outward direction within a body lumen; and
   an inverted membrane attached at a first end to the support hoop and at a second end to the proximal tubular member, said inverted membrane having a proximally tapered proximal section and an enlarged diameter distal section, the junction between the enlarged diameter distal section and the proximally tapered proximal section forming a folded or creased portion wherein a length of the inverted membrane folds back and extends outwardly from the enlarged diameter distal section and proximally terminating at the support hoop;
   wherein the proximally tapered proximal section of the inverted membrane is attached to the proximal tubular member and extends through the support hoop to the folded or creased portion.

2. The embolic protection filter of claim 1, further including a plurality of retrieval struts each having a proximal end and a distal end, the proximal end attached to the proximal tubular member, the distal end attached to the support hoop.

3. The embolic protection filter of claim 1, wherein a portion of said filter frame is secured to the guidewire.

4. The embolic protection filter of claim 1, wherein said guidewire further includes a distal stop, and wherein the filter frame is slidably and rotationally disposed about the guidewire.

5. The embolic protection filter of claim 1, wherein said plurality of expandable struts are biased to self-expand within the body lumen.

6. The embolic protection filter of claim 1, wherein said plurality of expandable struts are formed of a metal.

7. The embolic protection filter of claim 6, wherein said metal is nickel-titanium alloy.

8. The embolic protection filter of claim 1, wherein said inverted membrane is a microporous membrane.

9. The embolic protection filter of claim 8, wherein said microporous membrane is comprised of a polymeric material.

10. The embolic protection filter of claim 9, wherein said polymeric material is selected from the group consisting of polypropylene, polyvinylchloride, polyamide, polyurethane, polyester, polyethylene tetraphlalate, polyether-ether ketone, polyether block amide and polytetrafluoroethylene.

11. The embolic protection filter of claim 1, wherein said inverted membrane comprises a mesh screen.

12. The embolic protection filter of claim 11, wherein said mesh screen is formed of a metal.

13. The embolic protection filter of claim 12, wherein said metal is selected from the group consisting of stainless steel, nickel-titanium alloy and platinum.

14. The embolic protection filter of claim 1, wherein said support hoop has a pre-formed shape.

15. The embolic protection filter of claim 1, further comprising a delivery sheath having an inner lumen adapted to contain the embolic protection filter in a collapsed position.

16. The embolic protection filter of claim 1, wherein the tapered proximal section of said inverted membrane is disposed proximal the support hoop.

17. The embolic protection filter of claim 1, wherein said inverted membrane is substantially conical in shape.

18. The embolic protection filter of claim 1, wherein the proximal tubular member is ecured to the guidewire.

\* \* \* \* \*